United States Patent
Kiselev

(10) Patent No.: US 8,697,123 B2
(45) Date of Patent: Apr. 15, 2014

(54) MEDICATION ON THE BASIS OF 3,3'-DIINDOLYLMETHANE (DIM) WITH HIGH-BIOAVAILABILITY AND ITS USE IN TREATMENT OF HUMAN HYPERPLASTIC AND INFLAMMATORY DISEASES

(75) Inventor: Vsevolod Ivanovich Kiselev, Moscow (RU)

(73) Assignee: Zakrytoye akstionernoye obschestvo "VELES FARMA", Moscow (RU)

( * ) Notice: Subject to any disclaimer, the term of this patent is extended or adjusted under 35 U.S.C. 154(b) by 0 days.

(21) Appl. No.: 13/643,425

(22) PCT Filed: Mar. 5, 2011

(86) PCT No.: PCT/RU2011/000141
§ 371 (c)(1),
(2), (4) Date: Oct. 25, 2012

(87) PCT Pub. No.: WO2011/136691
PCT Pub. Date: Nov. 3, 2011

(65) Prior Publication Data
US 2013/0039979 A1    Feb. 14, 2013

(30) Foreign Application Priority Data
Apr. 26, 2010  (RU) .............................. 2010116353

(51) Int. Cl.
A61K 9/48      (2006.01)
B01F 17/00     (2006.01)
A61K 9/10      (2006.01)
A61K 31/404    (2006.01)
A61K 35/60     (2006.01)

(52) U.S. Cl.
CPC .............. A61K 9/10 (2013.01); A61K 9/4891 (2013.01); A61K 31/404 (2013.01); A61K 35/60 (2013.01)
USPC ................ 424/463; 516/9; 548/469; 424/555

(58) Field of Classification Search
None
See application file for complete search history.

(56) References Cited

U.S. PATENT DOCUMENTS 6,231,887 B1   5/2001   Gao et al.
6,416,793 B1   7/2002   Zeligs et al.
6,689,387 B1   2/2004   Zeligs

FOREIGN PATENT DOCUMENTS

RU    2202346           4/2003
RU    2318509           3/2008
WO    WO 2006/105196    10/2006
WO    WO 2009/032699    3/2009

OTHER PUBLICATIONS

International Search Report of PCT/RU2011/000141, date of mailing Jul. 28, 2011.
McCarty, MF et al Multifocal angiostatic therapy: an update Integr. Cancer Ther., Nov. 11, 2005, 4(4): 301-314 (ISR).

(Continued)

Primary Examiner — Bethany Barham
(74) Attorney, Agent, or Firm — Collard & Roe, P.C.

(57) ABSTRACT

The invention relates to medicine and chemico-pharmaceutical industry. A medication for treating human hyperplastic and inflammatory diseases containing 3,3'-diindolylmethane as an active agent and a carrier containing a mixture of cod-liver oil and at least one polysorbate at the following proportions of the components in mass %:

| | |
|---|---|
| 3,3'-diindolylmethane | 1-20 |
| cod-liver oil | 10-20 |
| polysorbate | the balance. |

6 Claims, 7 Drawing Sheets

(56) References Cited

OTHER PUBLICATIONS

Dalessandri K.M., Firestone G.L., et al. (2004), Pilot Study: Effect of 3-Diindolylmethane Supplements on Urinary Hormone Metabolites in Postmenopausal Women with a History of Early-Stage Breast Cancer. Nutrition and Cancer, 50(2), 161-167. (Spec. pp. 2-3).

Kim E.J., Park S.Y., et al. (2007), Activation of Caspase-8 Contributes to 3,3'- Diindolylmethane-Induced Apoptosis in Colon Cancer Cells, J of Nutrition, 137, 31-36. (Spec., p. 3).

Auborn K.J. (2002), Therapy for Recurrent Respiratory Papillomatosis, Antiviral Therapy, 7(1), 1-9. (Spec., p. 4).

MEDICATION ON THE BASIS OF 3,3'-DIINDOLYLMETHANE (DIM) WITH HIGH-BIOAVAILABILITY AND ITS USE IN TREATMENT OF HUMAN HYPERPLASTIC AND INFLAMMATORY DISEASES

CROSS REFERENCE TO RELATED APPLICATIONS

This application is the National Stage of PCT/RU2011/000141 filed on Mar. 5, 2011, which claims priority under 35 U.S.C. §119 of Russian Application No. 2010116353 filed on Apr. 26, 2010, the disclosure of which is incorporated by reference. The international application under PCT article 21(2) was not published in English.

FIELD OF THE INVENTION

The invention relates to medicine and chemico-pharmaceutical industry.

BACKGROUND OF THE INVENTION

Medications based on indole compounds derived from the Cruciferous family that includes cabbages, Brussels sprouts, cauliflower, and broccoli, and also synthetic analogues thereof are used extensively in medical practice today. Interest toward compounds in this group of compounds is explained, in particular, by their anti-carcinogenic and anti-estrogenic properties that make them suitable for treating diseases of the female reproductive system organs and certain hormone pathologies accompanied by hyperplastic processes. The most widespread diseases in this category include mastopathies, uterine myomas, endometriosis, adenomyosis, dysplasia of the uterine cervix of various etiologies, and hyperplasia of the thyroid.

Tumors of the reproductive organs are first in the structure of oncological morbidity among women, and morbidity increases by an average 1% a year. Tumors are second in the structure of mortality, and mortality "growth rates" (28%) remain the highest. According to WHO experts, about a million mammal cancer cases are registered around the world every year, a third of them with a lethal outcome. In the estimates of some researchers, five million women around the world will be suffering from this malignant tumor in the coming decade.

It is common knowledge that reproductive organ tissues are exposed continuously to the effect of a great variety of factors that stimulate active division (proliferation) and induce the start of specific signal cascades. These include three principal intracellular mechanisms that cause activation of cellular proliferation: (1) hormonal (or estrogen-dependent) mechanism; (2) mechanism induced by growth factors; and (3) mechanism activated by pro-inflammatory cytokines.

The involvement of estrogens in the development of neoplastic processes in hormone-dependent tissues (epithelium of mammary glands, endometria, and uterine cervix) is commonly recognized today and is viewed as one of the primary etiological factors for their development.

The pathogenetic mechanism of hyperplastic processes developing in the mammary gland have been studied well in our days. Obviously, by blocking the main signal transduction channels of signals stimulating proliferation of mammary gland cells, we can expect to be successful in preventing and treating pathological cases arising on this basis. In other words, pharmacological correction of hyper-proliferation diseases of reproductive system organs is to be undertaken at all stages and in respect of all signal cascades mediating key pathophysiological functions.

Many years of endeavors to find natural compounds blocking development of hyperplastic processes in hormone-dependent issues have, at last, resulted in success. Indole-3-carbinol (I3C) phytonutrient is one of these compounds that is contained in cruciferous vegetables (various kinds of cabbages). I3C provides protection against tumors owing to the broad spectrum of its biological activities. The clinical effect of I3C in various pathologies depends significantly on the individual specifics of the drug taking patients' metabolism, in particular, their ability to convert I3C to its various derivatives that, in turn, can interact synergistically and/or antagonistically (Dalessandri K. M., Firestone G. L., et al. (2004), Pilot Study: Effect of 3-Diindolylmethane Supplements on Urinary Hormone Metabolites in Postmenopausal Women with a History of Early-Stage Breast Cancer. *Nutrition and Cancer*, 50(2), 161-167).

3,3'-Diindolylmethane (DIM) is one of the derivatives produced by indole-3-carbinol upon oligomerization. This compound displays virtually all biological effects inherent in indole-3-carbinol, including its capacity to influence positively changes in the ratios of estrogen metabolites. DIM, however, is not transformed metabolically in the human organism and is a stable chemical compound. These distinctions of indole-3-carbinol from diindolylmethane make DIM a more preferable choice in pharmaceutical compositions with other pharmacologically active substances for treating hyperplastic and proliferative diseases.

DIM can be used to treat various inflammatory diseases (WO 2006105196, published on Oct. 5, 2006).

DIM has been found to induce proapoptotic death of cell with disturbed metabolism. In particular, DIM activates one of key apoptosis enzymes, Caspase-8, causing the death of transformed cells of intestinal cancer (Kim E. J., Park S. Y., et al. (2007), Activation of Caspase-8 Contributes to Diindolylmethane-Induced Apoptosis in Colon Cancer Cells, *J of Nutrition*, 137, 31-36). We assumed that the ability of DIM to activate apoptosis mechanisms can also extend to cells infected with intracellular microorganisms, in particular, *Chlamydia Trachomatis*. Chlamydial infection is very widespread and, in the view of many researchers, is one of the principal causes of female infertility. Antibiotics is a traditional therapy to treat chlamydial cervicitis. And yet, the infecting agent cannot be eradicated completely in almost 30% to 40% of the cases at the end of the treatment course, which causes the disease to recur. The reason is that the life cycle of *Chlamydia Trachomatis* consists of several stages, one of which, "inclusion bodies," is resistant to antibiotics. This explains the insufficient efficiency of antibiotic therapy.

Researchers have been attempting to develop formulations having high diindolylmethane absorption.

In particular, a prior art pharmaceutical composition developed for treating mastopathy and endometriosis (U.S. Pat. No. 6,689,387 published on Feb. 10, 2004) consists of microparticles of I3C or 3,3'-diindolylmethane in a starch matrix, such as, for example, solid drug formulations for oral administration. These formulations contain 30% to 70% of starch that improves active agent solubility without giving them sufficient stability in storage.

DIM formulations on the basis of pegylated vitamin E are known in prior art (U.S. Pat. No. 6,416,793 published on Jul. 9, 2002). TPGS-based compositions, though, have helped achieve a very insignificant (not more than 50% to 100%) increase in biological availability of DIM, its analogues, and derivatives, for which reason the therapeutic potential of these compounds cannot be used to capacity. Besides, the preparation has to be spray-dried in a very power-intensive process that raises its production costs.

The closest prior art of the present invention described in international application WO 2009032699 (published on Mar. 12, 2009) relates to pharmaceutical compositions based on an anti-proliferative combination of DIM, polyunsaturated fatty acids (PUFAs), and folic acid. These compositions are disadvantageous because they are not stable enough, the principal component precipitating as tiny crystals in storage. Moreover, most people being short of omega-3 fatty acids, derived PUFAs may only have exaggerated effects. According to recent findings, addition of folic acid is undesirable for small children having inflammatory diseases of the autoimmune type.

Notably, indole derivatives have proved to be effective in pediatric practice. In particular, indole-3-carbinol and 3,3'-diindolylmethane are used extensively to treat respiratory papillomatosis of the larynx in young children (Auborn K. J. (2002), Therapy for Recurrent Respiratory Papillomatosis, *Antiviral Therapy,* 7(1), 1-9). Solid drug formulations are hard to divide into doses. Clinical practice requires liquid drug formulations that can be dosed accurately in 1 milligram per 1 kilogram of weight.

SUMMARY OF THE INVENTION

It is an object of this invention to:

(1) develop drug formulations on the basis of 3,3'-diindolylmethane that are effective treatment for chronic inflammatory and hyperplastic processes and have maximum bioavailability and allow active agent concentration in the patients' blood to exceed significantly 200 ng in a milliliter of blood; and (2) develop a liquid 3,3'-diindolylmethane drug formulation easy to dose in pediatric practice.

This object is achieved in a new drug formulation of 3,3'-diindolylmethane.

The new formulation is a solution containing an active agent—3,3'-diindolylmethane—and a cod-liver oil carrier, and also at least one polysorbate at the following proportions of the components in mass %:

| | |
|---|---|
| 3,3'-diindolylmethane | 1-20 |
| cod-liver oil | 10-20 |
| polysorbate | the balance. |

Maximum bioavailability and stability in storage are achieved by selecting cod-liver oil and polysorbate as carrier in specified proportions.

Polysorbates are surfactants that are emulsifiers and solubilizers (solvents) of fats for, as a rule, water-base drugs. Polysorbate numbers (20, 40, 60, and 80) are related to types of fatty acids bonded to some molecules (coco oil acids are related to polysorbate 20, palm oil acids, to polysorbates 40 and 60, and olive oil acids, to polysorbate 80). Any polysorbates or mixtures thereof may be used according to the claimed invention. It is preferred, though, to use polysorbate 80 or polysorbate 20.

Polyunsaturated fatty acids capable, concurrently with arachidonic acid, of biosynthesis of mostly vasodilatory prostaglandins and leukotrienes having a lower thrombogenic activity (EPA and DHA) in cod-liver oil are insufficiently concentrated to have a therapeutic effect, for which reason they increase DIM bioavailability if used as carrier, but do not produce the desired effects.

The solution can be packed in dark-glass flasks, or in capsules. It is a tradition to pack oil-base drug formulations in soft gelatin capsules. Such capsules are not air-tight, however, and DIM is oxidized gradually and the concentration of the main agent reduced as a result. It is preferred, therefore, to use solid gelatin capsules coated with hydroxypropyl methyl cellulose or a phthalate thereof. A possible choice is, for example, Licaps capsules developed by Capsulgel company. Solutions can be packed in these capsule in argon and sealed off by laser.

The drug is also intended to treat hyperplastic and inflammatory diseases in humans. Examples of diseases in which the claimed drug is useful to prescribe include myoma, adenomyosis, hyperplasia of the thyroid, atopic dermatitis, Crohn's disease, and other inflammatory intestinal diseases, papillomatosis of the larynx, and chlamydial cervicitis. The drug is preferably administered at a rate of 0.5 to 2 mg of 3,3'-diindolylmethane per kilogram of the patient's weight. Depending on the severity of the disease, age, gender, and attending pathologies, the doses may be increased or decreased.

BRIEF DESCRIPTION OF THE DRAWINGS

The invention is explained in the following drawings.

DESCRIPTION OF THE PREFERRED EMBODIMENTS OF THE INVENTION

Figure 1:
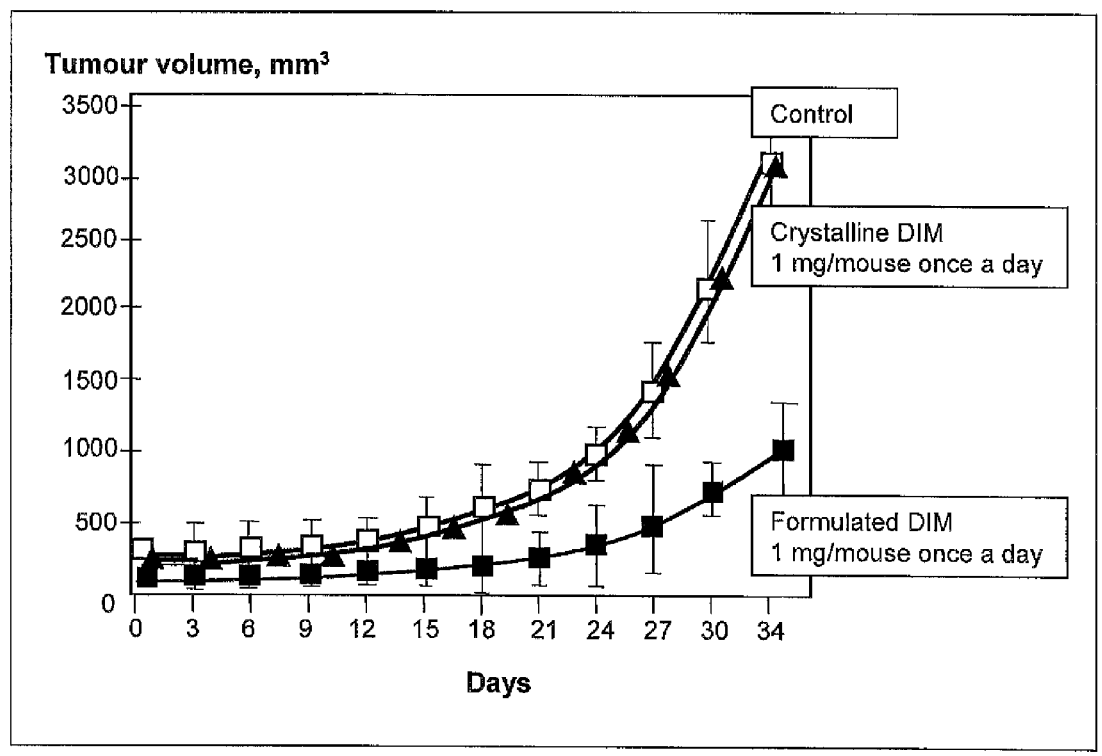
FIG. 1 shows growth dynamics of inoculated MCF-7 tumor in mice having no thymus (nu/nu) C57Black/6 in control (–□–) and following intrastomachic administration of the claimed drug to the animals (–■–), and preparations on the basis of crystalline DIM (–▲–)

The invention is illustrated with the following examples of the specific embodiments thereof:

Example 1

A Method for Producing a Soluble Drug Formulation of 3,3'-diindolylmethane of High Bioavailability (DIM-High Bioavailability (DIM-HB)).

Cod-liver oil was added to a polysorbate (or a mixture of polysorbates) at a rate of 10% to 20% of the total composition mass, and the resultant mixture was stirred carefully until a uniform fluid was obtained. 3,3'-Diindolylmethane was added to the resultant solution at a rate of 1% to 20% (10 to 200 mg of the substance per 1 g of the composition) and stirred until it dissolved completely. The resultant solution was packed in special-purpose capsules or dark-glass flasks.

Example 2

Drug Formulations on the Basis of 3,3'-diindolylmethane.
A. Capsules containing 100 mg of 3,3'-diindolylmethane, 100 mg of cod-liver oil, and 80 to 400 mg of polysorbate.
B. Capsules containing 50 mg of 3,3'-diindolylmethane, 50 mg of cod-liver oil, and 80 to 400 mg of polysorbate.
C. Capsules containing 20 mg of 3,3'-diindolylmethane, 80 mg of cod-liver oil, and 80 to 450 mg of polysorbate.
D. 10 ml dark-glass flasks containing a solution of concentrated 3,3'-diindolylmethane 10 mg per 1 g of the solution, 10% of cod-liver oil, and a mixture of polysorbate 20 and polysorbate 40 making up the balance.
E. 50 ml dark-glass flasks containing a solution of concentrated 3,3'-diindolylmethane 100 mg per 1 g of the solution, 15% of cod-liver oil, and polysorbate 80 making up the balance.

Example 3

Experimental Study of Specific Pharmacological Activity of the Claimed Drug In Vivo.

A week before tumor cells were inoculated to female mice having no thymus (nu/nu) line C57Black/6, a pill containing 0.72 mg of estradiol from which the hormone is released within 60 days was implanted in the subscapular area of the mice.

To induce solid tumors, tumor cells of human mammary gland adenocarcinoma line MCF-7 were collected with 0.05% solution of Tripsin-EDTA (Sigma, U.S.) and rinsed three times with a sterile phosphate salt buffer (PBS), whereupon 3 million cells in 0.1 ml of physiological salt solution were injected subcutaneously in the side area of each experimental animal (the number of live cells were counted with trypan blue (0.1%) and light microscope).

The claimed medication of Example 2, item D, was introduced intrastomachically (through a probe) in an equivalent of 1 mg per one mouse in the test group (10 animals in the group) every day 24 hours after inoculation of xenogeneic mammal tumor cells. Physiological salt solution was administered to control animals.

The size of solid tumors was measured once every two or three days after they appeared.

The quantity of DIM in the blood plasma of mice line C57Black/6 was determined by the HPLC method on a System Gold liquid chromatograph (from Beckman, U.S.) using a UV detector at a variable wavelength.

The claimed medication in an equivalent of 20 mg of DIM/kg was administered intrastomachically (through a probe) to test group animals (36 animals in the group in all) and individual I3C at a rate of 250 mg of DIM/kg (30 animals in the group) to obtain blood samples. Physiological salt solution was administered to the control animals. At time points of 0.25, 0.5, 0.75, 1.0, 1.5, 2.0, 4.0, 6.0, 12.0, 18.0, 24.0, and 36.0 hours after administration of the claimed formulation and 0.25, 0.5, 0.75, 1.0, 1.5, 2.0, 4.0, 6.0, 12.0, and 24.0 hours after administration of individual DIM, peripheral blood was withdrawn by a heparinized syringe from the tail vein of the test animals (three animals at each time point). Each blood sample was placed in a heparin-containing test tube. The blood samples were centrifuged (at 10,000×g for 5 minutes), whereupon 1.5 to 2.0 ml of plasma was withdrawn, frozen, and stored at minus 20° C.

Immediately before the HPLC analysis, an internal standard, 4-methoxy-indole (IS) (2.5 µl of solution at concentration of 0.4 mg/ml) was added to the experimental blood samples of 250 µl in volume, stirred by Vortex, and allowed to stand at room temperature for 30 minutes, whereupon the samples were extracted twice by tertbutyl methyl ester (750 µl).

The organic phase was separated in each sample from the aqueous phase by centrifuging (2,800×g for 10 minutes) and transferred to a new 4 ml test tube. The organic layers of the samples were combined for each experimental time point, the ester was vaporized in nitrogen flow, and 150 µl of eluent (acetonitrile/50 mM of Hepes buffer at a volume ratio of 40 to 60, and pH of 7.4) was added to the residue, and 50 µl of the resultant sample was placed in a chromatograph.

Similar procedures were carried out on control blood plasma samples, to which specified quantities of diindolylmethane were added within the range of concentrations of 0.05 to 10.0 µg/ml.

The quantity of DIM in the blood plasma was determined on a System Gold (Beckman, U.S.) liquid chromatograph with an UV detector at a wavelength of 280 nm.

Liquid chromatography was conducted at room temperature (22° C. to 24° C.) on a Nucleosil column, C18.5 µm (4.6×50 mm). The eluent (mobile phase) consisted of water and acetonitrile (AC). The mobile phase was degassed and filtered prior to chromatography. Elution was conducted at the AC concentration gradient in the following sequence: (1) 15% to 60% of AC within the first 20 minutes; (2) linear AC gradient 60% to 65% from the 20th to 40th minute; (3) linear AC gradient 65% to 85%, from the 40th to 65th minute; and (4) repeated column balancing by 15% of AC for 5 minutes. Elution had a total duration of 70 minutes and an elution rate of 1 ml/min.

DIM concentration in experimental samples was measured on calibration graphs showing the relationship between the concentration of these substances and areas of chromatographic peaks.

The method used in the HPLC analysis had a sensitivity of 0.05 µg/ml.

The antineoplastic efficiency of these compounds was assessed by measuring the size of the solid tumor in experimental and control groups of animals.

FIG. 1 shows that, beginning with approximately day 12 from the start of the experiment, the control group animals that were not given the claimed drugs showed intensive growth in the size of solid tumors. Over the next 20 days (day 14 to day 34 of the experiment), the average size of the tumor induced by cells of human adenocarcinoma of line MCF-7 increased approximately 10-fold. Over the same time, the average tumor size in animals given the claimed drug increased fivefold only.

Administration of the claimed drug to mice having no thymus (nu/nu) C57Black/6 in a 1 mg dose slowed down significantly the growth of solid tumors induced by inoculation of the animals with human mammal tumor cells of line MCF-7. Moreover, if used in doses specified, the claimed drug did not cause any changes in the cellular morphology of the liver, kidneys, and other functionally important organs nor had it any effect on the weight of the experimental animals.

It may be concluded, therefore, that the claimed drug has a pronounced antineoplastic effect against mammal cancer in vivo on the xenotransplantation animal model.

Histological studies of the tissues of animals (killed under ether narcosis at the end of the experiment) given the claimed drug have shown that the drug used in doses specified does not cause any changes in the cellular morphology of the liver, kidneys, and other functionally important organs and does not have any effect on the weight of the experimental animals.

Example 4

Concentration of 3,3'-diindolylmethane (μg/ml) in the Blood Plasma of Experimental Animals Given 200.0 mg/kg of 3,3'-diindolylmethane Substance Intrastomachically.

Figure 2:
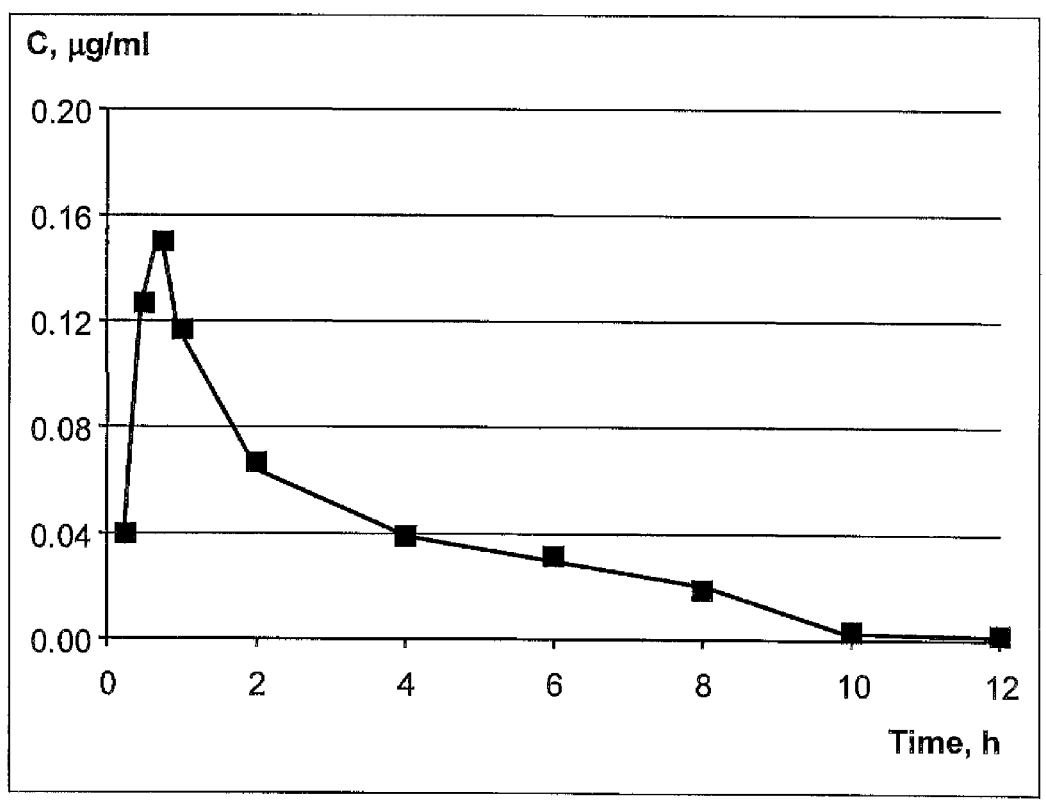
FIG. 2 shows averaged dynamics in the concentration of DIM in the blood plasma of the experimental animals upon intrastomachic administration of DIM at a rate of 200.0 mg/kg (in linear coordinates)
Figure 3:
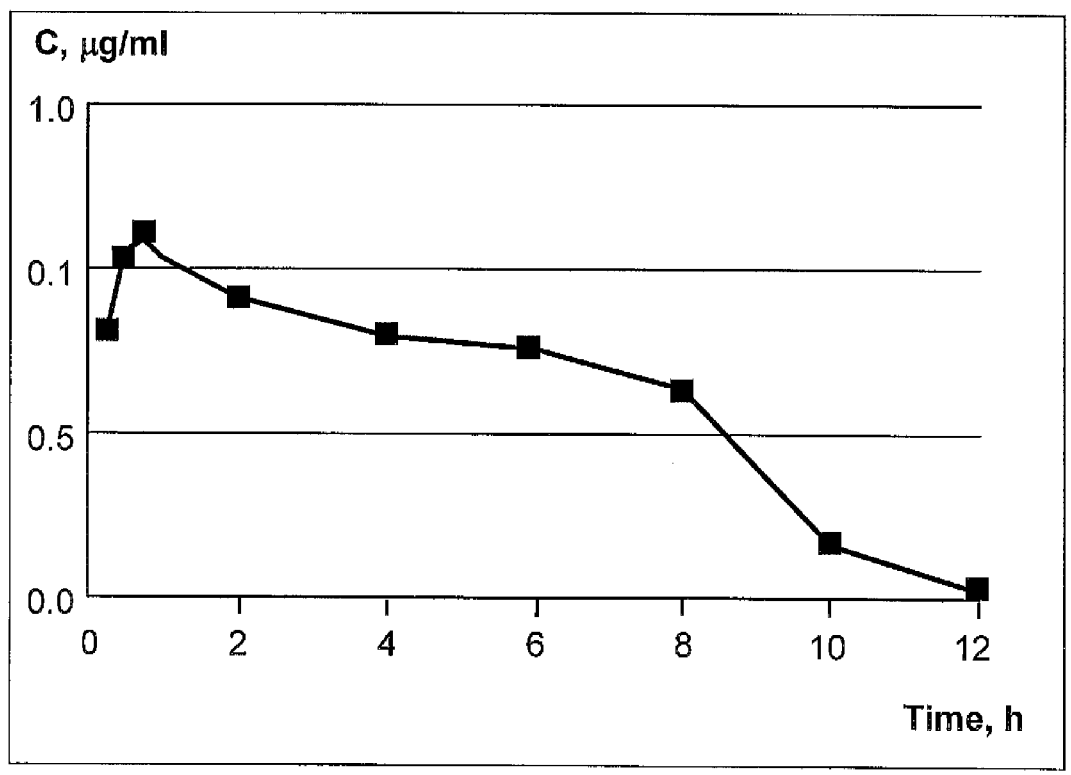
FIG. 3 shows averaged dynamics in the concentration of DIM in the blood plasma of experimental animals upon intrastomachic administration of DIM at a rate of 200.0 mg/kg (in logarithmic coordinates)

The results of measurements of 3,3'-diindolylmethane substance concentration in the blood plasma of rats given the substance intrastomachically are shown in Table 1. The averaged pharmacokinetic curves are shown in FIG. 2 and FIG. 3.

TABLE 1

| Nos. | Blood sampling time, hour | | | | | | | |
|---|---|---|---|---|---|---|---|---|
|  | 0.25 | 0.5 | 1.0 | 2.0 | 4.0 | 6.0 | 8.0 | 12.0 |
| 1 | 0.05 | 0.13 | 0.17 | 0.12 | 0.07 | 0.04 | 0.03 | <0.03 |
| 2 | 0.05 | 0.12 | 0.15 | 0.12 | 0.06 | 0.03 | 0.03 | <0.03 |
| 3 | 0.04 | 0.11 | 0.16 | 0.10 | 0.07 | 0.04 | 0.03 | <0.03 |
| 4 | 0.03 | 0.12 | 0.13 | 0.11 | 0.06 | 0.05 | 0.04 | <0.03 |
| 5 | 0.04 | 0.13 | 0.15 | 0.13 | 0.06 | 0.04 | 0.03 | <0.03 |
| 6 | 0.03 | 0.15 | 0.14 | 0.12 | 0.08 | 0.03 | 0.03 | <0.03 |
| Arithmetic mean | 0.04 | 0.13 | 0.15 | 0.12 | 0.07 | 0.04 | 0.03 | <0.03 |
| Mean error | 0.00 | 0.01 | 0.01 | 0.00 | 0.00 | 0.00 | 0.00 | 0.00 |
| Standard deviations | 0.01 | 0.01 | 0.01 | 0.01 | 0.01 | 0.01 | 0.00 | 0.0 |
| Coefficient of variation | 22.36% | 10.79% | 9.43% | 8.85% | 12.25% | 19.97% | 12.27% |  |
| Median | 0.04 | 0.13 | 0.15 | 0.12 | 0.07 | 0.04 | 0.03 |  |
| Geometric mean | 0.04 | 0.13 | 0.15 | 0.12 | 0.07 | 0.04 | 0.03 |  |

Following administration, 3,3'-diindolylmethane in the system blood flow was measured every 15 minutes, the maximum concentration being observed about 1 hour on (0.13 to 0.17 μg/ml), 3,3'-Diindolylmethane concentration then started falling gradually, to a minimum (less than 0.03 μg/ml) 12 hours after administration. Individual values had a moderate spread, with the coefficient of variation CV ranging between 8% and 22%.

Example 5

3,3'-diindolylmethane Concentration (μg/ml) in the Blood Plasma of Experimental Animals Given 0.10 mg/kg of High-Bioavailability 3,3'-diindolylmethane Intrastomachically.

Figure 4:
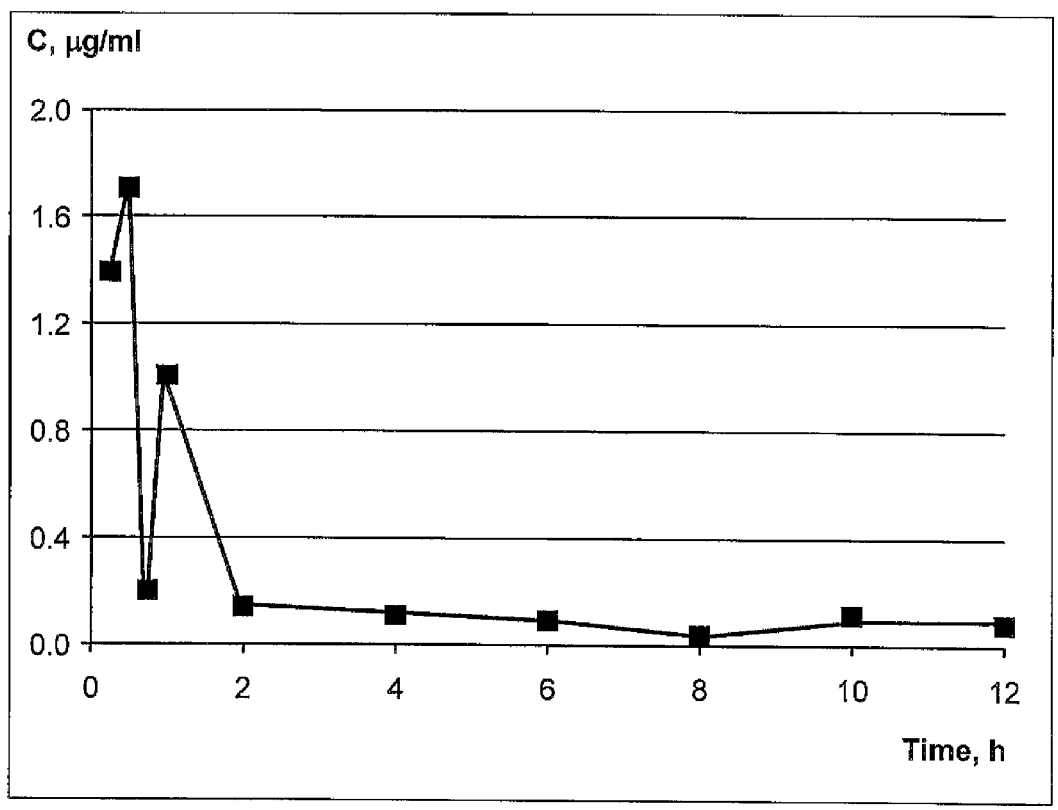
FIG. 4 shows averaged dynamics in the concentration of DIM in the blood plasma of experimental animals upon intrastomachic administration of DIM capsules of high bioavailability at 0.10 mg/kg (in linear coordinates)
Figure 5:
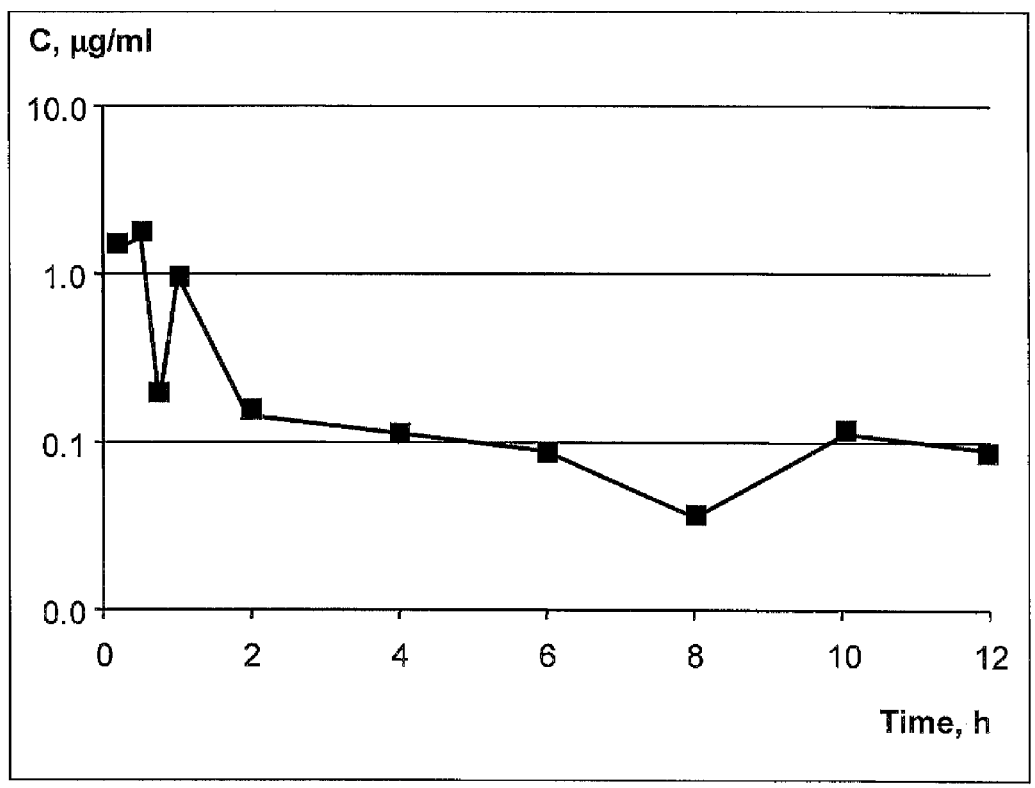
FIG. 5 shows averaged dynamics in the concentration of DIM in the blood plasma of experimental animals upon intrastomachic administration of DIM capsules of high bioavailability at 0.10 mg/kg (in logarithmic coordinates)

The results of measurements of 3,3'-diindolylmethane substance concentration in the blood plasma of rats given the substance intrastomachically are shown in Table 2. The averaged pharmacokinetic curves are shown in FIG. 4 and FIG. 5.

TABLE 2

| Nos. | Blood sampling time, hour | | | | | | | |
|---|---|---|---|---|---|---|---|---|
|  | 0.25 | 0.5 | 1.0 | 2.0 | 4.0 | 6.0 | 8.0 | 12.0 |
| 1 | 1.38 | 1.70 | 0.20 | 0.98 | 0.15 | 0.12 | 0.11 | 0.04 |
| 2 | 1.52 | 1.61 | 0.19 | 1.10 | 0.16 | 0.11 | 0.07 | 0.03 |
| 3 | 1.29 | 1.65 | 0.25 | 1.06 | 0.12 | 0.10 | 0.09 | 0.03 |
| 4 | 1.40 | 1.88 | 0.18 | 0.93 | 0.14 | 0.11 | 0.10 | 0.04 |
| 5 | 1.12 | 1.59 | 0.16 | 0.88 | 0.14 | 0.11 | 0.11 | 0.05 |
| 6 | 1.64 | 1.80 | 0.23 | 1.08 | 0.14 | 0.11 | 0.07 | 0.03 |
| Arithmetic mean | 1.39 | 1.71 | 0.20 | 1.01 | 0.14 | 0.11 | 0.09 | 0.04 |
| Mean error | 0.07 | 0.05 | 0.01 | 0.04 | 0.01 | 0.00 | 0.01 | 0.00 |
| Standard deviations | 0.18 | 0.11 | 0.03 | 0.09 | 0.01 | 0.01 | 0.02 | 0.01 |
| Coefficient of variation | 12.95% | 6.68% | 16.42% | 8.85% | 9.38% | 5.75% | 20.02% | 22.27% |
| Median | 1.39 | 1.68 | 0.20 | 1.02 | 0.14 | 0.11 | 0.10 | 0.04 |
| Geometric mean | 1.38 | 1.70 | 0.20 | 1.00 | 0.14 | 0.11 | 0.09 | 0.04 |

Following administration, 3,3'-diindolylmethane was measured in the system blood flow every 15 minutes, the maximum concentration being observed 30 minutes on (1.6 to 1.8 μg/ml), and concentration then dropped by a factor of eight, followed two hours after administration by another concentration maximum (0.9 to 1.1 μg/ml). 3,3'-Diindolylmethane concentration then started to fall gradually, until 12 hours after administration diindolylmethane was measured in the blood in minimum quantities (about 0.03 μg/ml). Individual values had a moderate spread, with the coefficient of variation CV ranging between 5% and 20%.

A significant fact is that the dosage of the DIM formulation developed per animal is smaller by a factor of 2,000 than it is for crystalline DIM.

These differences in dosages regardless, DIM concentration in the blood plasma of the experimental animals is comparable for the two preparations.

Example 6

Efficiency of the Claimed Drug in Atopic Dermatitis Treatment.

We had under observation 43 atopic dermatitis patients aged between 18 and 25, including 35 men (81.4%) and eight women (18.9%). Skin manifestations of the disease accorded with the clinical pattern of atopic dermatitis having a morphology and eruption localization typical of this dermatosis. The patients were found to have the following clinical forms of atopic dermatitis (AD): 34 patients (78.3%) had erythematous-squamous AD with mild or moderate lichenification, one patient (2.3%) has lichenoid AD, 2 patients (4.6%) had pruriginous AD, and six patients (13.8%) had eczematous AD. Severity of the disease was assessed by the SCORAD index, ranging from 12.4 to 61.2. Of the total number, 27 patients (62.8%) had a mild form, 15 patients (34.9%) had a moderate form, and one patient (2.3%), a heavy form. White diffuse persistent dermographism was manifest in 44% of the patients. All patients complained of itching of varying intensity, from insignificant to bioptic. Itching was admitted by 35 patients (81.4%) to be moderate and tolerable, and intolerable by eight patients. A majority, or 37 patients (86%), complained of irritability, low mood, fatigue, and sleeping disorders. A majority of patients (90.7%) had ups and downs in their disease. AD exacerbations were most frequent during the cold time of the year. The factors provoking a successive exacerbation included departures from hypoallergenic dieting for 27 patients (62.8%), stress for eight patients (18.6%), infectious diseases for five patients (11.6%), and drug taking for four AD patients (9.3%).

The new preparation was used to treat the patients. 3,3'-Diindolylmethane in liquid formulation of high bioavailability was the active agent of the preparation.

The preparation was used in capsules containing 10, 20, 50, and 100 mg of the active agent. All patients were given the preparation dosed at 1 mg per 1 kg of body weight a day.

The therapeutic results were assessed on the basis of changes in the clinical picture on the seventh and 14th days of treatment and one month from the start of treatment. Dynamics in the skin disease symptoms assessed on the SCORAD scale served as objective criteria.

Among the 43 patients who had taken the preparation, clinical convalescence from itching and inflammatory skin changes was achieved in ten patients (23.3%) experiencing a light form and nine patients (20.9%) having medium severity within an average two weeks from the start of therapy. Eight patients (18.6%) in the mild form and five patients (11.6%) in medium severity form showed significant improvement. Another seven patients (16.3%) in the light form and one patient (2.3%) in high severity form showed positive response to the therapy by improving. No therapeutic effect was observed in two patients (4.6%) in the mild form and one patient (2.3%) in medium severity form. The preparation had a clinical efficiency of 74.4%.

Cytokine Production

Flow-through cytometry was used to determine the production rate of the tumor necrosis factor $\alpha$ (TNF-$\alpha$) and interferon $\gamma$ (IFN-$\gamma$) on beads covered with antibodies of cytokines in atopic dermatitis patient before and after treatment.

Figure 6:
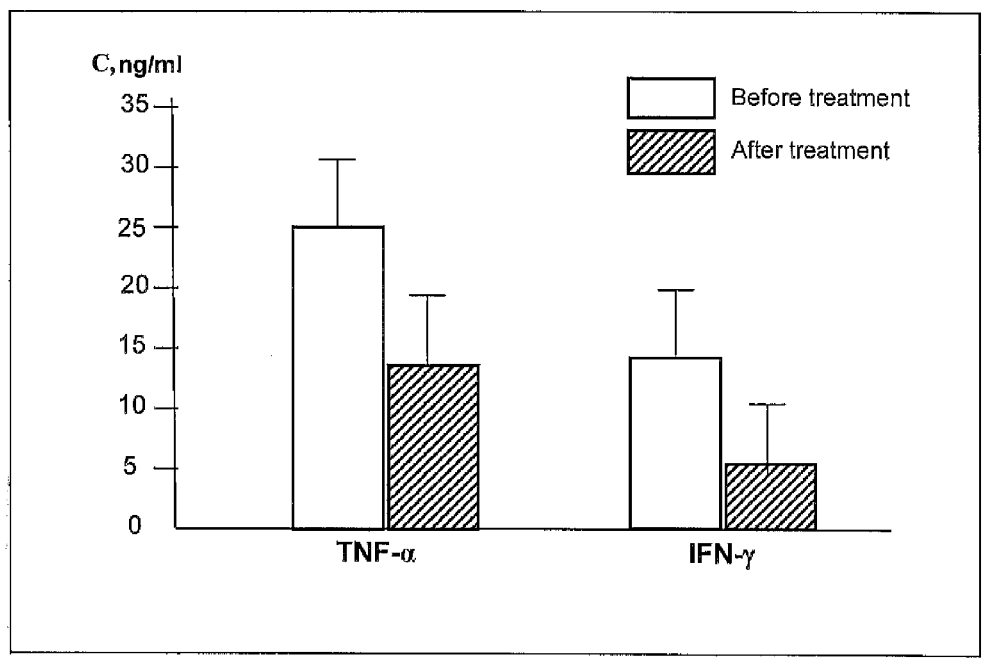
FIG. 6 shows production of cytokines by peripheral blood lymphocytes of atopic dermatitis patients before and after treatment.

Authentic (t-test, $p<0.05$) reduction in TNF-$\alpha$ and IFN-$\gamma$ production was observed after treatment (FIG. 6).

IgE Production

Figure 7:
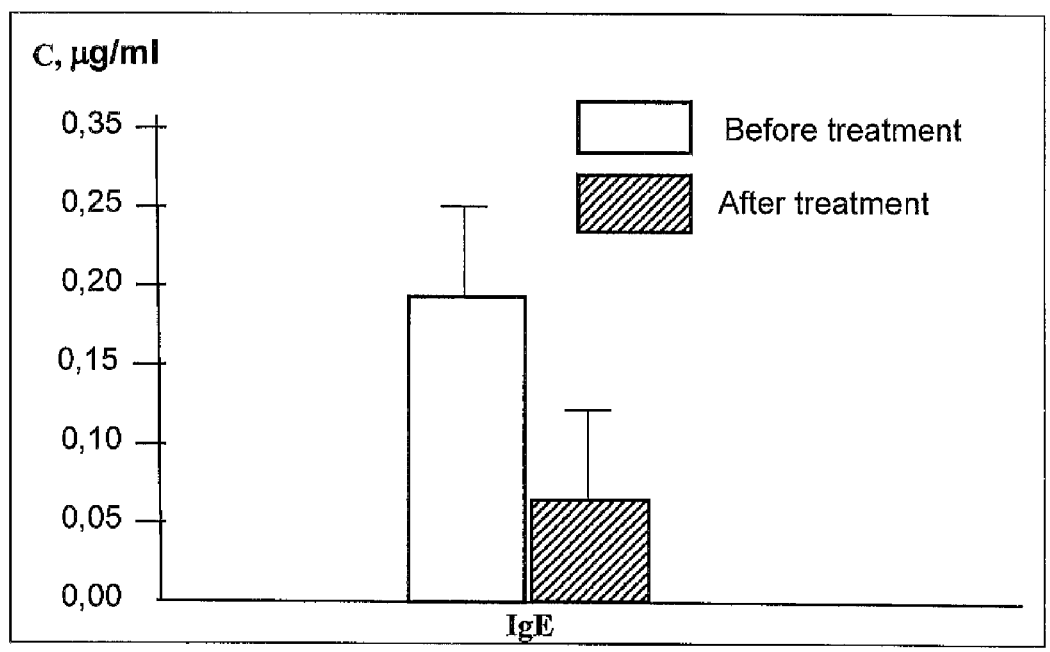
FIG. 7 shows the effect of treatment of atopic dermatitis patients at the total IgE level in the serum.

Treatment with the preparation resulted in an authentic reduction in the IgE level, a fact that is observed but rarely in this disease. The patients had another blood sample taken 1.5 to 2 months after treatment. Immunoglobulins in the blood serum have a lifetime of about one month. Accordingly, reduction in the IgE level in the AD patients' blood serum after treatment means a direct effect the preparation has on IgE production. IgE reduction was observed in 100% of the cases, even if low from the start (FIG. 7).

Example 7

Clinical Efficiency of the New DIM Formulation for Preventing Recurrences of Crohn's Disease.

Purpose

Determining the efficiency of the new DIM formulation in maintaining Crohn's disease remission was the purpose of the study.

Study Structure

Randomized double-blind placebo-controlled study of one-year direction.

Patients

The study covered 58 patients (aged 18 to 67, 50% of them male) suffering from Crohn's disease in the clinical remission stage, though with a high risk of recurrence. Laboratory tests revealed a chronic inflammatory process. The exclusion criteria included age of <18 or >75 years; mesalamine, sulfasalazine, or corticosteroids taken during the preceding three months, or immunosuppressive medications taken over the preceding six months.

Treatment

The patients were given DIM in 50 mg capsules (Example 2, item B) or placebo two or three times a day.

Assessment Criteria

Frequency of recurrences and duration of remission. A recurrence was determined by a 100 point increase in Crohn's disease activity index from the basic level, remaining at a level of >150 points for two weeks.

Principal Results

Treatment with DIM in 50 mg capsules lowered the frequency of recurrences in comparison with placebo (28% and 69%, respectively; $p<0.001$).

Conclusion:

Treatment with DIM in 50 mg capsules reduces the frequency of recurrences and maintains Crohn's disease remission in the absence of clinical manifestations of the disease, with increased content of inflammation markers in the blood.

Example 8

Study of DIM Concentration in Patients' Blood Plasma

All classical studies compared the efficiencies of DIM-HB and crystalline DIM in equal doses. All study groups of patients showed pronounced positive dynamics in response to DIM-HB treatment and no dynamics at all when given crystalline DIM.

These differences are probably attributed to effective therapeutic DIM concentrations reached in the peripheral blood and target tissues in response to DIM-HB treatment. Measurement results of these parameters are shown in Table 3.

TABLE 3

| Preparation | Dose | Clinical efficiency | DIM concentration in the plasma |
|---|---|---|---|
| Crystalline DIM | 10 mg | − | Not measured |
| DIM-HB | 10 mg | + | Over 100 ng/ml |
| Crystalline DIM | 100 mg | − | 20-30 ng/ml |
| DIM-HB | 100 mg | + | Over 300 ng/ml |

We established through our observations that stable clinical effects were achieved by administering DIM-HB in doses of 100 mg a day. In this case, DIM concentration in the plasma topped 300 ng/ml in response to 100 mg of DIM-HB.

Example 9

DIM-HB Administered to Women Having Hyperplastic Processes in the Endometrium.

The study involved 32 patients at an average age of 47.3±1.53 years, who refused to have hormonal therapy and who had no indications for surgery.

The patients were given 50 mg of DIM-HB twice a day for six months.

Efficiency was assessed at the end of three and six months from clinical data, hormone level, ultrasonography, separate diagnostic curettage, and cervical endometrium biopsy. The results are shown in Table 4.

TABLE 4

| Indications | Before treatment, % | After 3 months of treatment, % | After 6 months of treatment, % |
| --- | --- | --- | --- |
| Menorrhagia (excessive menstruation) | 65.6 | 56.3 | 34.4 |
| Metrorrhagia | 46.9 | 28.1 | 15.6 |
| Pain in lower abdomen related to the menstrual cycle | 28.1 | 18.8 | 15.6 |
| Pre- and post-menstrual blood discharges | 21.9 | 21.9 | 12.5 (scanty) |

Example 10

Results of Clinical Studies of DIM-HB Efficiency in Treatment of Patients Having a Combined Pathology of Adenomyosis and Myoma of the Uterus.

The study involved 72 patients suffering from the disease for 10 years and averaging 38.5±2.7 years of age.

The patients were selected on the following criteria:
1. Patients who refused to take hormonal preparations on early manifestations of the disease.
2. Patients who had an earlier therapy without effect.
3. Patients having no indications for surgery.

The patients were treated with 50 mg of DIM-HB twice a day for six months.

The dynamics of clinical symptoms of patients with a combined pathology of adenomyosis and uterine myoma after six months of treatment are shown in Table 5.

TABLE 5

| Indications | Before treatment, % | After treatment, % |
| --- | --- | --- |
| General weakness, increased fatigue, reduced work capacity | 21.7 | 4.3 |
| Hyperpolymenorrhea | 65.2 | 10.9 |
| Dysmenorrhea | 45.7 | 8.7 |
| Premenstrual blood discharges | 39.1 | 10.9 |
| Acyclic bleeding | 10.9 | 2.2 |
| Pain in lower abdomen unrelated to the menstrual cycle | 48 | 17 |
| Dyspareunia | 10.9 | 2.2 |
| Functional disorder of adjacent organs | 19.6 | 6.5 |
| Mastalgia | 76.1 | 8.7 |
| Uterus volume | 522.7 ± 60.2 cm$^3$ | 480 ± 55.8 cm$^3$ |
| Thickness of the uterus back wall affected by adenomyosis | 29.4 mm | 25.2 mm |

Example 11

Change in the Level of Molecular Markers in the Uterine Myoma Nodes After DIM-HB Administration in Comparison with Control.

The study involved 24 patients with indications for surgery, which had been put off for various reasons.

DIM-HB was administered in doses of 50 mg twice a day for 3.5 months.

The results of immuno-histochemical studies (assessment in points by the semiquantitative method according to the percentage of colored cells (Colvin R. et al., 1995) ($p<0.05$)) are shown in Table 6.

TABLE 6

| Process | Marker | Increase ↑ Decrease ↓ |
| --- | --- | --- |
| Proliferation | Ki-67* | ↓ 4.3 |
|  | PCNA | ↓ 3.8 |
|  | C-myc | ↓ 4.5 |
|  | FGF | ↓ 1.9 |
|  | IGF-I | ↓ 9.2 |
| Proliferation, | EGF (EGFR) | ↓ 2.4 |
| angiogenesis | PDGF | ↓ 2.3 |
| Apoptosis | Bcl-2 | ↓ 8.0 |
|  | ApopDETEK** | ↑ 5.5 |
| Angiogenesis | CD-34 | ↓ 5.9 |

*count of the percentage of colored nuclei per 3,000 cells.

**count of the percentage of detected dead corpuscles per 3,000 cells.

Example 12

Study of the Efficiency of Treatment Given to Persons with Thyroid Pathology with the DIM-HB-Base Preparation.

For the purposes of this study, the efficiency of treatment received by 138 persons was subjected to clinico-biochemical analysis. One group (Group I) of patients included patients who were treated with a preparation based on DIM-HB in doses between 10 mg and 100 mg a day. A second group comprised patients who received standard treatment. The efficiency of treatment of Group I patients with the DIM-HB-base preparation is shown in Table 7.

TABLE 7

| Nosology | Number of patients studied | Efficiency after 3 mo. | Efficiency after 12 mo. | Side effect of the preparations |
| --- | --- | --- | --- | --- |
| Diffuse goiter I-III deg. | 68 | 52 | 68 | There was no negative side effect in all cases. |
| Nodular goiter | 47 | 21 | 47 | Positive side effect was observed in respect of functions of other organs |
| Diffuse toxic goiter | 9 | 9 | 9 | |
| Idiopathic hypothyroidism | 14 | 3 | 14 | |

An analysis of treatment efficiency in the first group showed improvements in all respects. In hypothyroidism cases in which patients received (before turning to medics) standard treatment, DIM-HB treatment helped them gradually to go off, or reduce significantly the dose of, L-thyroxine (or its analogues).

Treatment efficiency in Group II patients (standard therapy) is shown in Table 8.

TABLE 8

| Nosology | Number of patients | Treatment method | Efficiency after 3 mo. | Efficiency after 12 mo. | No effect after 12 mo. | Side effect of the preparations Number of patients | Side effect of the preparations Description |
|---|---|---|---|---|---|---|---|
| Diffuse goiter II-III deg. | 73 | Thyroidal hormones. Iodine preparations | 56 | 64 | 9 | 17 | Exacerbation of chronic hepatocholicestitis, myocardial cardiosclerosis, CPN, allergy, pharmacological thyrotoxicosis |
| Nodular goiter | 43 | Thyroidal hormones | 20 | 25 | 18 | 7 | High arterial blood pressure, tachycardia, attack of chronic cholecystopancreatitis |
| Diffuse toxic goiter | 19 | Cytostatics | 16 | 16 | 3 | 4 | Leukopenia, headache, strumogenic effect, edematous syndrome |
| Idiopathic hypothyroidism | 17 | Substitutive therapy with thyroidal hormones + iodine preparations + calcium | 13 | 17 | | 4 | Pharmacological thyrotoxicosis (in one case), dysfunction of the cardiovascular system |

Conclusions:

Treatment with DIM-HB-based preparations as an independent method to treat thyroidal pathology helps achieve positive clinical results; their efficiency is confirmed by laboratory and instrumental studies.

The benefit of using these preparations to treat thyroidal pathologies consists in a steady clinical effect, without harm to other organs (no side effects). These preparations can help achieve positive dynamics in hypothyroidism treatment (as substitutive therapy is gradually abandoned or doses are reduced); avoid surgery in many instances, and normalize the thyroidal structure and function in cases of diffuse toxic goiter and nodular goiter.

Example 13

Therapy Against Recurrence of Respiratory Papillomatosis of the Larynx with a DIM-HB-Base Preparation.

A DIM-HB-base preparation of Example 2, item D, was given in a dose of 1 mg per 1 kg of a child's weight. The preparation was administered once to three times during meals. Treatment was given for at least 12 weeks. Therapy was started after the latest removal of papillomas.

The length of the period between recurrences was analyzed before and after administration of the preparation.

The efficiency of treatment was assessed according to the following criteria:

prolonged remission (no papilloma growth observed for two or more years);

increase in the period between recurrences (the time period between surgeries to remove papillomas increased by 50% or more from the pretreatment period); and no effect was registered (the time period between surgeries did not change or changed by less than 50% of the pretreatment period).

Exclusion criteria for the study included unauthorized termination of treatment with the DIM-HB-base preparation (two patients) and a short observation period (the observation period between the start of preparation taking and analysis of treatment results was shorter than the pretreatment period between recurrences for seven patients).

The results of anti-recurrence therapy of recurrent respiratory papilloma (RRP) with the preparation given to 46 patients were analyzed. These 46 patients showed early symptoms of the disease at ages 1 to 156 months (an average of 44.7±29.38 months). The age of the first surgery to remove papillomas ranged between 2 and 162 months (an average of 56.7±29.26 months).

Prior to treatment with the preparation, the children underwent between 2 and 64 operations to remove papillomas (an average of 13.4±9.01). The length of the period between recurrences prior to treatment with the preparation varied from two weeks to 12 months (an average of 5.6±2.26 months). The patients' age at the start of treatment was between 2 and 14 years (an average of 8.9±3.49 years).

Results:

Pronounced positive effect of anti-recurrence treatment with the preparation was registered in 41 patients (89.1%), in 21 (45.6%) of whom a lengthy remission (from 2 years to 3 years 10 months of observation) was achieved, and in the other 20 (43.4%) the length of the period between recurrences increased by 50% to sixfold.

No side effects of the treatment undertaken were observed at all.

Example 14

Activity in Respect of Chlamydial Cervicitis.

Thirty women diagnosed with "chlamydial cervicitis" were selected for testing. One group (15 patients) was given standard treatment with antibiotics (250 mg of Surnamed twice a day). The other group (15 patients) was also given 50 mg of DIM (Example 2, item B) three times a day. After 30 days of treatment, samples taken from the cervical canal were studied by the polymerase chain reaction for *Clamydia Trachomatis*. In the first group, nine women registered negative in laboratory testing, while in the second group, *Clamydia Trachomatis* was not detected in 14 women.

Conclusion:

Using high-bioavailability DIM-base preparations for treating chlamydial cervicitis helps induce apoptosis of infected cells and increase the efficiency of treatment.

Example 15

Stability Study of DIM Formulations Produced as Described in Example 1.

Soft gelatin capsules and solid gelatin capsules Licaps were used for preparing drug formulations. The capsules were stored at room temperature, and the quantity of the DIM active agent was measured at specified intervals by high-pressure chromatography.

The results of this study are shown in Table 9.

TABLE 9

| Capsule type | DIM dose | DIM content after storage at room temperature | | | |
|---|---|---|---|---|---|
| | | 30 days | 60 days | 90 days | 120 days |
| Soft | 50 mg | 40 mg | 35 mg | 30 mg | 28 mg |
| Solid (Licaps) | 50 mg | 50 mg | 50 mg | 50 mg | 50 mg |

The results of the study show that the quantity of the DIM active agent did not change in the solid gelatin capsules Licaps, while the concentration of the DIM substance decreased in the soft gelatin capsules because of DIM oxidation.

What is claimed is:

1. A medication for treating human hyperplastic and inflammatory diseases containing 3,3'-diindolylmethane as an active agent and a carrier, said medication being a solution containing a mixture of cod-liver oil and at least one polysorbate as the carrier with the following proportions of the components in mass %:

| | |
|---|---|
| 3,3'-diindolylmethane | 1-20 |
| cod-liver oil | 10-20 |
| polysorbate | the balance. |

2. The medication as claimed in claim 1, packed in dark glass flasks.

3. The medication as claimed in claim 1, packed in solid gelatin capsules coated with hydroxypropyl methyl cellulose or a phthalate thereof.

4. The method of administration of the medication as claimed in claim 1 for treating human hyperplastic and inflammatory diseases.

5. The method of administration as claimed in claim 4, wherein the medication is administered in doses of 0.5 to 2 mg of 3,3'-diindolylmethane per kilogram of a patient's weight.

6. The method of administration as claimed in claim 4, wherein said diseases are diseases in the group of myoma, adenomyosis, thyroid hyperplasia, atopic dermatitis, Crohn's disease, papillomatosis of larynx, and chlamydial cervicitis.

* * * * *